(12) United States Patent
Blachford et al.

(10) Patent No.: US 10,477,957 B2
(45) Date of Patent: Nov. 19, 2019

(54) ORAL CLEANING IMPLEMENT WITH A TOOL ADAPTED FOR REMOVAL OF DENTURE ADHESIVE FROM DENTURES

(71) Applicant: GlaxoSmithKline Consumer Healthcare (UK) IP Limited, Brentford, Middlesex (GB)

(72) Inventors: Marcus James Blachford, Warwickshire (GB); Alexander James Brian, Surrey (GB); Richard Brian Clough, Warwickshire (GB)

(73) Assignee: GlaxoSmithKline Consumer Healthcare (UK) IP Limited, Brentford, Middlesex (GB)

( * ) Notice: Subject to any disclaimer, the term of this patent is extended or adjusted under 35 U.S.C. 154(b) by 0 days.

(21) Appl. No.: 15/578,303

(22) PCT Filed: Jun. 7, 2016

(86) PCT No.: PCT/IB2016/053326
§ 371 (c)(1),
(2) Date: Nov. 30, 2017

(87) PCT Pub. No.: WO2016/199012
PCT Pub. Date: Dec. 15, 2016

(65) Prior Publication Data
US 2018/0140084 A1    May 24, 2018

(30) Foreign Application Priority Data
Jun. 8, 2015 (GB) .................. 1509862.7

(51) Int. Cl.
*A46B 15/00* (2006.01)
*A45B 5/00* (2006.01)
(Continued)

(52) U.S. Cl.
CPC ............ *A46B 15/0081* (2013.01); *A46B 5/00* (2013.01); *A61C 17/036* (2013.01); *A46B 2200/1066* (2013.01); *A46B 2200/1073* (2013.01)

(58) Field of Classification Search
CPC .. A46B 5/00; A46B 5/02; A46B 5/023; A46B 5/026; A46B 9/04; A46B 15/00;
(Continued)

(56) References Cited

U.S. PATENT DOCUMENTS 1,487,075 A * 3/1924 Olson ................ A46B 15/0055
132/309
1,519,515 A * 12/1924 Stonehill ............ A46B 15/0055
132/309
(Continued)

FOREIGN PATENT DOCUMENTS

CA    2147698    * 10/1996
CH    207272    * 10/1939
(Continued)

*Primary Examiner* — Mark Spisich
(74) *Attorney, Agent, or Firm* — Roshni A. Sitapara; Joshua C. Sanders

(57) ABSTRACT

Aspects of the present invention are directed to an oral cleaning implements having a head and a handle. The implements distal end of the handle may be a tool adapted for removal of denture adhesive from dentures.

16 Claims, 2 Drawing Sheets

(51) Int. Cl.
*A46B 5/00* (2006.01)
*A61C 17/00* (2006.01)

(58) Field of Classification Search
CPC ............ A46B 15/0055; A46B 15/0069; A46B 15/0075; A46B 15/0081; A46B 2200/1066; A46B 2200/1073; A61C 17/036
USPC .......... 15/105, 110, 111, 117, 167.1; 132/309
See application file for complete search history.

(56) References Cited

U.S. PATENT DOCUMENTS

| | | | | |
|---|---|---|---|---|
| 1,784,986 A | * | 12/1930 | Eisenberg | A46B 15/0055 132/309 |
| 2,083,217 A | * | 6/1937 | Brothers | A46B 5/007 132/309 |
| 2,464,321 A | * | 3/1949 | Konczal | A46B 9/026 15/104.001 |
| 4,449,934 A | * | 5/1984 | Salam | A61C 17/00 132/309 |
| 5,564,148 A | | 10/1996 | Prevost et al. | |
| 5,778,475 A | * | 7/1998 | Garcia | A46B 15/0055 15/111 |
| 7,182,542 B2 | * | 2/2007 | Hohlbein | A46B 11/0003 401/132 |
| 2002/0162183 A1 | * | 11/2002 | Cho | A46B 9/06 15/167.1 |
| 2013/0263397 A1 | | 10/2013 | Hohlbein et al. | |

FOREIGN PATENT DOCUMENTS

| | | | |
|---|---|---|---|
| GB | 426997 A | | 4/1935 |
| GB | 555380 A | | 8/1943 |
| GB | 711017 | * | 6/1954 |
| JP | 2010-36004 | * | 2/2010 |

* cited by examiner

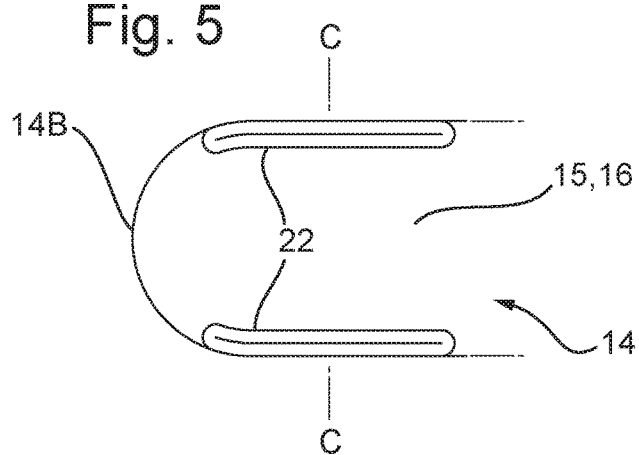
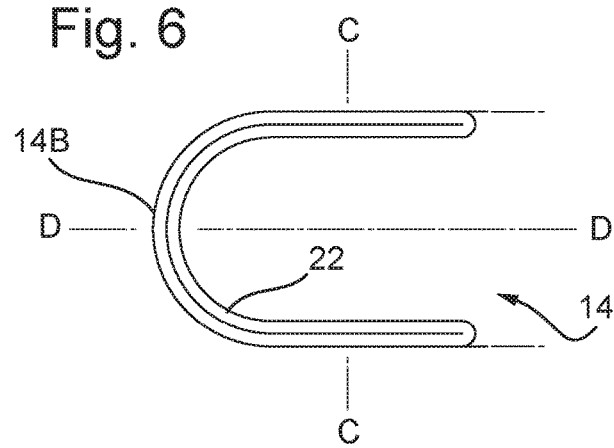
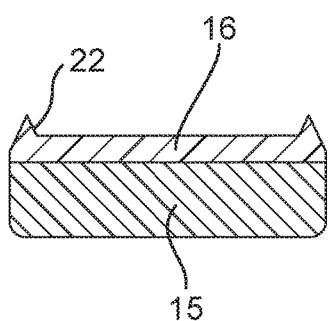
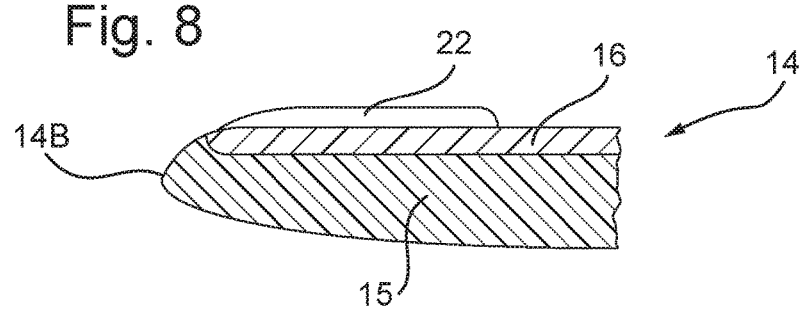

ORAL CLEANING IMPLEMENT WITH A TOOL ADAPTED FOR REMOVAL OF DENTURE ADHESIVE FROM DENTURES

This application is a 371 of International Application No. PCT/IB2016/053326, filed Jun. 7, 2016, which claims the priority of GB Application No. GB 1509862.7 filed Jun. 8, 2015, which is incorporated herein in its entirety.

This invention relates to oral cleaning implements, in particular to denture cleaning implements.

When using dentures it is common to use a denture adhesive to improve retention of the dentures in the mouth. An example of a denture adhesive is the product POLI-GRIP™ produced by GlaxoSmithKline. A problem with denture adhesives is that though it is desirable and recommended to remove residual denture adhesive from dentures after use, e.g. when the dentures are removed at the end of a day such residual denture adhesive can be difficult to remove. At present many denture users attempt to remove such residues using for example a conventional toothbrush such as the toothbrush they use for cleaning other parts of their dentures. If this does not succeed, or as their normal method, some denture users employ for example an abrasive pad, a kitchen utensil or even a fingernail etc. US-A-2005/191599 discloses a method of removing denture adhesive. US-A-2007/037717 discloses a solvent system for use with tissues for removing denture adhesive.

An object of this invention is therefore to meet the need for an improved means for removing denture adhesive from dentures, which is among other things more convenient and more hygienic than known methods. Other objects and advantages of the present invention will be apparent from the following disclosure.

According to the present invention an oral, i.e. tooth and/or denture, cleaning implement is provided comprising a head supporting oral cleaning elements, and an integral handle extending in a longitudinal direction between a proximal end adjacent to the head and a distal end remote from the head; characterised in that adjacent the distal end of the handle is a tool adapted for removal of denture adhesive from dentures.

The head may comprise an essentially conventional toothbrush head as well known in the art. Typically such heads are ca. 2.5-4 cm long, ca. 1-1.5 cm wide and 0.3-0.6 cm thick.

The oral cleaning elements are preferably of a type and in an arrangement which enables their use for cleaning dentures and/or natural teeth, either when the dentures are within the user's oral cavity or when the dentures have been removed for cleaning, or both. Suitable elements include conventional polyamide bristles as are well known in the art, arranged in tufts extending from a surface of the head. Such bristles may for example be conventionally end-rounded, or tapered, or a mixture of end-rounded and tapered bristles, for example an inner cluster of tufts of tapered bristles surrounded by an outer ring of tufts of non-tapered end rounded bristles. Additionally or alternatively the oral cleaning elements may comprise other known types of oral cleaning elements. Such elements may be located on the head in conventional arrangements such as tufts of bristles arranged in widthways or lengthways rows or in one or more polygonal cluster on a surface of the head. Such a head may also be used for cleaning natural teeth.

For cleaning dentures some users may use a technique involving holding the handle in such a way as to facilitate pressing a thumb or finger tip against the surface of the head opposite to that from which the oral cleaning elements extend, so as to increase the pressure with which the oral cleaning elements may be applied to the dentures. To facilitate this, in an embodiment, the surface of the head opposite to that from which the oral cleaning elements extend may be concave. Such a concave opposite surface can provide a more secure seat for the user's thumb or finger to reduce the possibility of slipping of the user's thumb or finger off the head during use. To further enhance the use of the head in this way the surface of the head opposite to that from which the oral cleaning elements extend may be coated with a grip enhancing material such as an elastomer material such as a thermoplastic elastomer (TPE) material. The use of such TPE materials on the handles of toothbrushes to enhance a user's grip is already known in the toothbrush art.

The handle too may be substantially the same size, shape and construction as a conventional toothbrush handle, having a thickness direction parallel to the direction in which the oral cleaning elements such as bristles extend, and a widthways direction perpendicular to the longitudinal and thickness directions. Typically such handles are ca. 18-20 cm long, ca. 1-1.5 cm wide and 1-1.5 cm thick.

It is well known in the toothbrush art to make toothbrush handles from two material components, typically one component being a hard plastic material such as polypropylene or other polymers, and the other component being a softer elastomer material such as a TPE material for example to enhance grip or aesthetic appearance. The handle of the present implement may be made in a similar construction.

Examples of TPE materials which have been used in this way in toothbrush handles include styrene-ethylene/butylene-styrene ("SEBS") copolymers with a typical hardness ShoreA 10-60, although hardness outside this range may be suitable, e.g. Santoprene™, Megol™ and others. Such two-component toothbrushes are disclosed for example in U.S. Pat. Nos. 5,054,154, 6,292,973, 5,735,012 and EP-A-0 336 641 among others. Normally such two component toothbrush handles are made by first making a skeleton of the hard plastic material, normally by injection moulding, having one or more cavity in the position(s) where the second component material is to be located. This skeleton is then enclosed in a further injection mould defining the shape of the second material part(s) and the second component being a thermoplastic elastomer is injected in to flow into and occupy the one or more cavity to thereby form the second component part(s) of the toothbrush. The implement of this invention may be made in an exactly analogous manner.

The tool is preferably made integrally of the material of the handle of the oral cleaning implement.

In an embodiment the handle may be a two component handle as described above comprising a hard plastic material component and a softer elastomer material component, preferably a TPE material, and the tool, or at least its outer surface part, may be made integrally of the material of the softer elastomer material component. For example the tool may be formed in a layer of the softer elastomer material second component over an underlying part of a skeleton of first component hard plastic material.

In an embodiment the tool may comprise a scoop adapted for removal of denture adhesive from dentures.

For example the tool may comprise a ridge, for example suitable for use as a scoop on the surface of the handle, preferably integrally made of the material of the handle, preferably with its height direction substantially in the thickness direction of the handle.

Typically such a ridge may have a V-shaped, U-shaped, semicircular or ogival profile in section cut in the height direction through the ridge.

In plan view looking in the thickness direction such a ridge may be straight or curved, for example curved in an arc with its convex side facing widthways outwardly of the handle, with the ridge aligned in, or having its principal direction components in, the longitudinal direction of the handle.

In an embodiment such a ridge may be located adjacent a widthways side of the handle adjacent the distal end.

In an embodiment two such ridges may be provided adjacent widthways opposite sides of the handle adjacent the distal end.

In another embodiment there may be a single ridge around the distal end of the handle and having part of its extent along widthways opposite sides of the distal end of the handle. For example in plan view such a single ridge may have a U-shape, semicircular, ogival or V-shape.

Such a ridge or ridges may be provided by the surface of the handle adjacent the distal end incorporating a concavity in its material, e.g. in the softer elastomeric material of a two-component handle, which is bounded along at least part of its perimeter, preferably along at least part of both its widthways opposite sides by the ridge. Such a concavity may be in widthways and/or longitudinal section a shallow saucer shape. The inner side of such a ridge may merge into the profile of the concavity, and the outer side of such a ridge may merge with a side surface of the handle.

Such a concavity may be bounded on its proximal side by a smooth continuum slope or a step in the thickness direction up to a greater thickness of the handle material. Such a concavity may for example in plan view be of a rounded shape, e.g. circular, oval, D-shape or ogival shape (i.e. a rounded shape tapering toward a rounded point) with a ridge on each of its widthways opposite sides. Other shapes are also encompassed.

A tool comprising such a ridge may extend ca. 1-3 cm from the distal end of the handle toward the proximal end of the handle, e.g. a handle of the same general shape, size and proportions of a conventional toothbrush handle. Such dimensions have been found convenient and effective for removing residual denture adhesive from dentures.

Therefore in a preferred embodiment, the handle is made of two components being a hard plastic material component and a softer elastomer material component, the tool is made integrally of the material of the softer elastomer material component, and comprises a concavity in the softer elastomer material component adjacent the distal end of the handle, bounded on both widthways opposite sides by a ridge made integrally of the softer elastomer material component of the handle.

The tool may be located on any surface of the handle of the implement, for example a surface facing in the thickness direction or facing in the widthways direction. Preferably the tool is located on a surface of the handle facing in the thickness direction, and more preferably on a surface facing in the thickness direction in which the oral cleaning elements extend.

To facilitate use of both the oral cleaning elements and a tool located on a surface of the handle facing in the thickness direction, for example on a surface facing in the direction in which the oral cleaning elements extend, the handle is preferably shaped to facilitate being ergonomically conveniently held by the user with the oral cleaning elements facing in directions 180° rotated about the longitudinal direction, and provided with grip-enhancing features located on one or other, but preferably on both of its surfaces facing in the thickness direction. Such grip-enhancing features may for example comprise concavities in the surface(s), and/or surface areas of grip enhancing material such as a TPE material.

To facilitate the implement resting stably on a surface such as a bathroom counter with its oral cleaning elements, and/or the tool, safely pointing away from that surface, the surface of the handle facing in the widthways direction away from the direction the oral may include a planar region. For example such a region may comprise a planar rim of a grip enhancing concavity in the surface as described above.

The oral cleaning implement of the present invention may be made by an injection moulding process in which the material(s) of the head and handle are injected into one or more mould cavity defining their shape. The oral cleaning elements such as tufts of bristles may thereafter be inserted into socket holes in the head. Alternatively the oral cleaning elements may be set into the head by injecting head material around them during the injection moulding process. Such processes are well known in the art of toothbrush manufacture.

For example in such a process for making the implement, the handle and/or head may comprise two material components being a hard plastic material and a softer elastomer material as described above, a skeleton of the hard plastic material may be made first, then this skeleton may be enclosed in a further injection mould defining the shape of the second material part(s) and the second component may be injected in to form the second component parts of the toothbrush, including the tool.

In use, the oral cleaning elements may be used to clean parts of the dentures, e.g. the teeth parts, in a manner analogous to the way a conventional toothbrush may be used. Before or after this, the tool may be used to remove or loosen residual denture adhesive off the dentures, for example by applying the ridge in a scraping action to remove or at least loosen residual denture adhesive, before washing the detached or loosened denture adhesive away with a cleaning fluid such as water.

The oral cleaning elements of the present implement may also be used by a user to clean his/her teeth in a manner analogous to the way a conventional toothbrush may be used.

The invention therefore further provides a method of removing a denture adhesive from a denture, using the tool of an implement as described herein. In particular the above-mentioned ridge may be brought into contact with residual denture adhesive on the dentures and used to apply force to the residual adhesive to remove it from the dentures.

The invention will now be described by way of example only with reference to the accompanying drawings, of which:

FIGS. 5 and 6 show plan views of alternative shapes of ridges.

FIG. 7 shows a cross section of the tool of the implement of FIG. 5 or 6 at the line C-C.

FIG. 8 shows a longitudinal sectional view of the tool of the implement of FIG. 5 at the line D-D.

Figure 1:
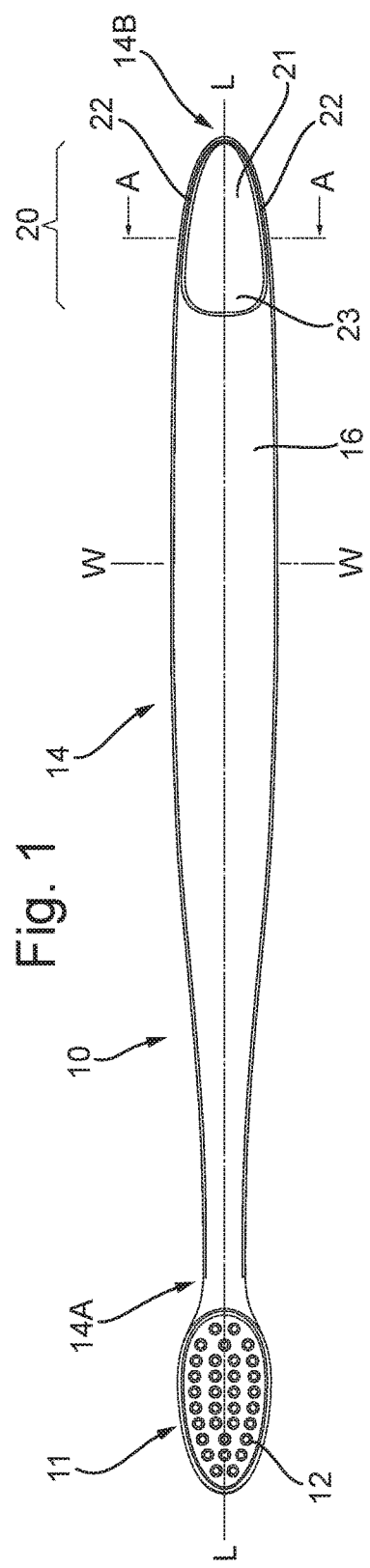
FIG. 1 shows a plan view of an oral cleaning implement of this invention.
Figure 2:
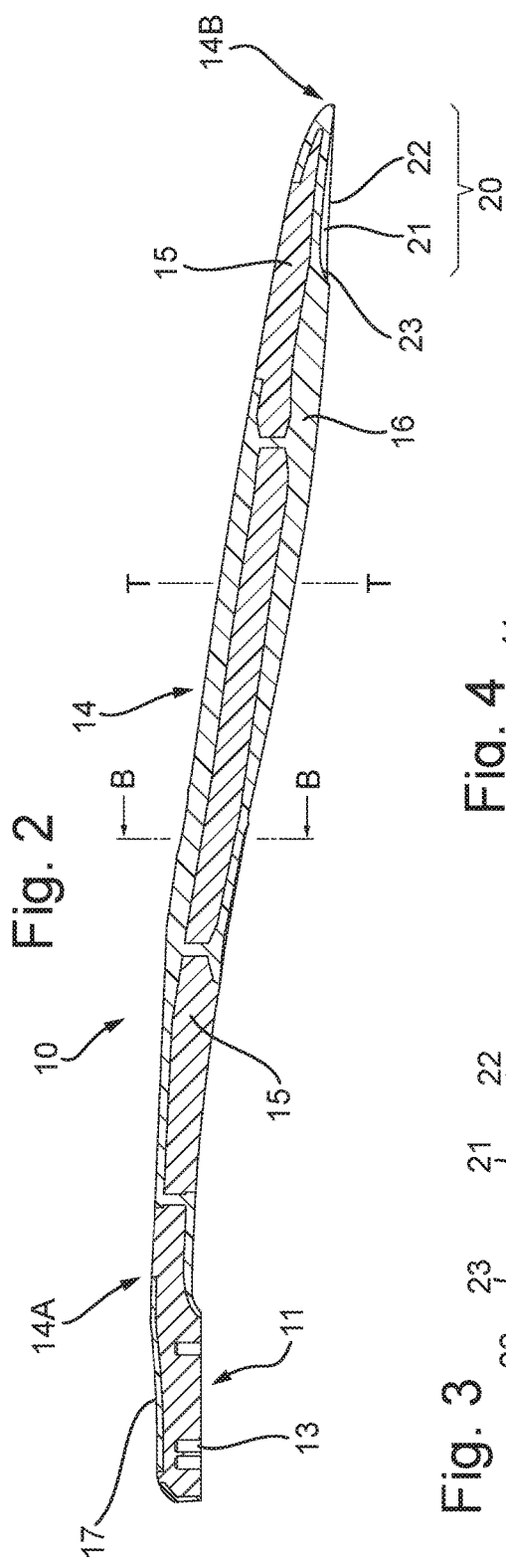
FIG. 2 shows a longitudinal sectional view of the oral cleaning implement of FIG. 1.
Figure 3:
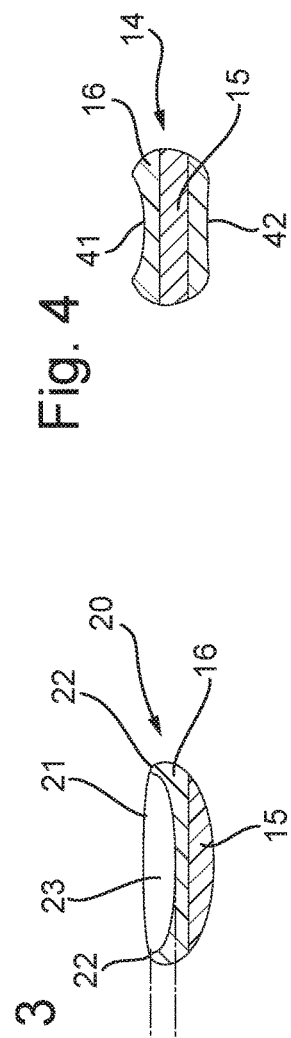
FIG. 3 shows a cross sectional view of the tool of the implement of FIGS. 1 and 2 at the line A-A looking in the direction of the arrow.

Referring to FIGS. 1, 2 and 3 an oral cleaning implement 10 overall is shown. This comprises a head 11 in the form of a conventional toothbrush head, supporting oral cleaning elements 12 being conventional bristles in tufts arranged in a conventional pattern, set in conventional socket holes 13 seen in FIG. 2.

The implement 10 also comprises an integral handle 14 extending in a longitudinal direction L-L between a proximal end 14A adjacent to the head 11 and a distal end 14B remote from the head 11. The handle 14 is substantially the same size, shape and construction as a conventional toothbrush handle and has a thickness direction T-T parallel to the direction in which the bristles 12 extend, and a widthways direction W-W perpendicular to the longitudinal L-L and thickness T-T directions. The head 11 and handle 14 are conventionally made of two material components, being a first component hard plastic material "skeleton" 15 seen in longitudinal section in FIG. 2, and a second component softer thermoplastic elastomer (TPE) material 16 occupying cavities in the skeleton 15 and forming the outer layer of parts of the handle 14, including around the distal end 14B.

The handle 14 has been made by a conventional process of first forming the skeleton 15 with cavities therein, then enclosing the skeleton 15 in an injection mould and then injecting the TPE material 16 into the injection mould so that the TPE flows into the cavities and forms the TPE parts 16 of the handle 14.

Adjacent the distal end 14B of the handle 14, on a surface of handle 14 facing in the thickness direction T-T in the same direction as the oral cleaning elements (tufts of bristles) 12, is a tool 20 adapted for removal of denture adhesive from dentures.

The tool 20 comprises a shallow saucer-profiled concavity 21 in the second component soft TPE material 16 bounded around the widthways part of its perimeter by two ridges 22 of the elastomer material 16 on the surface of the handle 14. As seen in plan view in FIG. 1 the ridges 22 are located adjacent the widthways opposite sides of the distal end 14B of handle 14 and follow the curved shape of the distal end 14B, being aligned substantially in the longitudinal direction L-L of the handle 14. At the distal end 14B of the handle 14 the ridges 22 merge smoothly into the surface profile at the distal end 14B of handle 14.

As seen in FIG. 3 each ridge 22 has a V-shaped profile in section as cut through in the widthways direction W-W, with its height in the thickness direction T-T of the handle. The inner profile of each ridge 22 merges smoothly into the saucer shaped curved profile of the concavity 21, and the outer profile of each ridge 22 merges into the widthways outer surface of the handle 14. Each ridge 22 is integrally formed with a layer of the TPE material 16 beneath ca. 0.5-2.5 mm thick, suitably ca. 1 mm thick, over the hard plastic material skeleton 15.

The concavity 21 is bounded on its proximal side by a step 23 of second component TPE material in the thickness direction T-T up to a greater thickness of the handle material 16. The maximum depth of the concavity 21, i.e. the height from the tops of the ridges 22 to their bottom, represented "d" in FIG. 3 is 1-2 mm. Ridges 22 of this height "d" over such an underlying thickness of TPE beneath are found suitable for use as a scoop for removing denture adhesive from dentures with minimal risk of damage to the dentures.

As seen in plan view in FIG. 1 the concavity 21 is of a rounded ogival shape, i.e. a rounded oval tapering toward the distal end 14B of the handle and corresponding to the overall ogival shape of the distal end 14B, with a ridge 21 on each of its widthways opposite sides.

The concavity 21 extends ca. 2.5 cm from the distal end 14B in the longitudinal direction L-L toward the proximal end 14A of the handle 14, and has a maximum width at the point where the step 23 begins of ca. 1.3 cm.

The concavity 21 with its side ridges 22 is able to function as a scoop for removing denture adhesive from dentures.

As seen most clearly in FIG. 2 the surface 17 of the head 11 opposite to that from which the oral cleaning elements 12 extend is concave in a shallow saucer shape corresponding in plan view in the thickness direction to the oval shape of head 11, with a maximum depth of 0.5-1.0 mm to provide a secure thumb- or finger-tip rest for a user. This surface 17 is also coated with a layer of the same TPE material 16 that forms parts of handle 14 over the underlying plastic material of the head.

Referring to FIGS. 5, 6, 7 and 8, these show alternative constructions of the distal end 14B of the handle 14 of the implement and of the tool 20. FIGS. 5 and 6 show plan views of the distal end 14B of the handle 14 of the implement 10 and this end 14B is rounded in a generally semicircular shape. In FIG. 5 two ridges 22 with their ends closest to the distal end curved in an arc with their convex side facing widthways outwardly of the handle 14 and having their principal direction components aligned in the longitudinal direction L-L of the handle, are provided adjacent widthways opposite sides of the handle 14. In FIG. 6 a single ridge 22 is provided which runs in a rounded shape around the distal end 14B of the handle 14, i.e. in a generally "U" shape as seen in plan with its convex side facing widthways outwardly of the handle 14 and having its limbs aligned in the longitudinal direction L-L of the handle. FIG. 7 is a section at C-C of either FIG. 5 or FIG. 6 through the distal end 14B cut across the longitudinal direction L-L of FIG. 1 showing how the ridges 22 are of a "V" shape in section.

FIG. 8 shows a sectional view as cut in the longitudinal direction L-L of FIG. 5 and shows that the ridges 22 extend for a short length along the handle 14, without the concavity of FIGS. 1 to 4, the upper surface of the handle 14 of the implement of FIG. 6 similarly being formed without the concavity of FIG. 1. At their end closest to the distal end 14B of the handle 14 the profile of the ridges 22 merges smoothly with the curved profile of the distal end 14B of the handle 14.

Figure 4:
FIG. 4 shows a cross section of the handle of the implement of FIGS. 1 and 2 at the line B-B looking in the direction of the arrow.

The handle 14 may be held by the user with the oral cleaning elements 12 facing in directions 180° rotated about the longitudinal direction, e.g. for using the elements 12 for cleaning teeth or dentures whilst in the mouth and after they have been removed from the mouth for cleaning. As seen in FIGS. 1 and 2, to facilitate this the handle 14 is provided with grip-enhancing features being areas of the TPE material 16 located on both of its surfaces facing in the thickness direction. Additionally as seen in FIG. 4 the handle 14 is provided with grip-enhancing features being a concavity 41 facing in the thickness direction opposite to the direction in which the oral cleaning elements 12 extend, and a concavity 42 facing in the opposite direction to the concavity 41, both concavities 41 and 42 being formed in the TPE material 16. These concavities 41, 42 are convenient finger and/or thumb rests for a user.

On the surface of the handle 14 opposite to the surface on which tool 20 is located is a planar region being the rim of the concavity 41. This region facilitates the implement 10 resting stably on a surface such as a bathroom counter with its oral cleaning elements 12 and tool 20 safely pointing away from that surface.

In use, the bristles 12 may be used to clean parts of the dentures (not shown) in a manner analogous to the way a conventional toothbrush may be used. Before or after this, the ridge 22 of tool 20 may be used to pick or scrape residual denture adhesive off the dentures, for example by applying the ridge 22 in a scraping action to remove or at least loosen residual denture adhesive, before washing the detached or loosened denture adhesive away with a cleaning fluid such as water.

The invention claimed is:

1. An oral cleaning implement comprising a head supporting oral cleaning elements, and an integral handle extending in a longitudinal direction between a proximal end adjacent to the head and a distal end remote from the head;
wherein adjacent to the distal end of the handle is a tool adapted for removal of denture adhesive from dentures;
wherein the handle is made of two components being a hard plastic material component and a softer elastomer material component, the tool is made integrally of the material of the softer elastomer material component, and comprises a concavity in the softer elastomer material component adjacent to the distal end of the handle, bounded on at least one widthways side by a ridge made integrally of the softer elastomer material component of the handle; and
wherein the tool comprises a scoop adapted for removal of denture adhesive from dentures.

2. An oral cleaning implement according to claim 1, wherein in plan view looking in the thickness direction, the ridge is curved in an arc with its convex side facing widthways outwardly of the handle, with the ridge having its principal direction components in the longitudinal direction of the handle.

3. An oral cleaning implement according to claim 2, wherein the ridge is located adjacent to the widthways side of the handle adjacent to the distal end.

4. An oral cleaning implement according to claim 2, wherein two such ridges are provided adjacent to widthways opposite sides of the handle adjacent to the distal end.

5. An oral cleaning implement according to claim 2, wherein there is a single ridge around the distal end of the handle and having part of its extent along widthways opposite sides of the distal end of the handle.

6. An oral cleaning implement according to claim 2, wherein the ridge or ridges is/are provided by the surface of the handle adjacent to the distal end incorporating the concavity in its material which is bounded along at least part of its perimeter by the ridge.

7. An oral cleaning implement according to claim 6, wherein the concavity is in plan view of a rounded shape, with a ridge on each of its widthways opposite sides.

8. An oral cleaning implement according to claim 7, wherein the rounded shape tapers toward the distal end of the handle.

9. An oral cleaning implement according to claim 1, wherein the tool extends circa 1-3 cm from the distal end of the handle toward the proximal end of the handle.

10. An oral cleaning implement according to claim 1, wherein the tool is located on a surface of the handle facing the thickness direction.

11. An oral cleaning implement according to claim 10, wherein the tool is located on a surface of the handle facing in the direction in which the oral cleaning elements extend.

12. An oral cleaning implement according to claim 1, wherein the oral cleaning elements comprise a mixture of end-rounded and tapered bristles.

13. An oral cleaning implement according to claim 1, wherein the surface of the head opposite to that from which the oral cleaning elements extend is concave.

14. A process for making an implement as claimed in claim 1, wherein it comprises an injection moulding process in which the materials of the head and handle are injected into one or more mould cavity defining their shape.

15. A process according to claim 14, wherein a skeleton of the hard plastic material is made first by injection moulding, then this skeleton is enclosed in a further injection mould defining the shape of the softer elastomer material component and the softer elastomer material component is injected in to form the softer elastomer material component of a toothbrush including the tool.

16. A method of removing a denture adhesive from a denture comprising: using the tool of an implement as claimed in claim 1 to remove denture adhesives from dentures.

* * * * *